(12) United States Patent
Darling et al.

(10) Patent No.: US 8,735,117 B2
(45) Date of Patent: May 27, 2014

(54) METHOD FOR MAKING ARTIFICIAL SCAFFOLD HAVING POROUS THREE-DIMENSIONAL BODY COMPRISING CELLS

(75) Inventors: Andrew Darling, Bradford, VT (US); Lauren Shor, Devon, PA (US); Wei Sun, Cherry Hill, NJ (US); Selcuk Guceri, Morrestown, NJ (US)

(73) Assignee: Drexel University, Philadelphia, PA (US)

( * ) Notice: Subject to any disclaimer, the term of this patent is extended or adjusted under 35 U.S.C. 154(b) by 706 days.

(21) Appl. No.: 12/877,818

(22) Filed: Sep. 8, 2010

(65) Prior Publication Data

US 2011/0165646 A1 Jul. 7, 2011

Related U.S. Application Data

(60) Division of application No. 11/842,796, filed on Aug. 21, 2007, which is a continuation-in-part of application No. PCT/US2006/006790, filed on Feb. 24, 2006.

(60) Provisional application No. 60/656,258, filed on Feb. 25, 2005, provisional application No. 60/656,505, filed on Feb. 25, 2005.

(51) Int. Cl.
| | | |
|---|---|---|
| *C12N 11/02* | (2006.01) | |
| *C12N 11/00* | (2006.01) | |
| *C12N 11/14* | (2006.01) | |
| *C12N 11/08* | (2006.01) | |
| *C12N 11/04* | (2006.01) | |
| *C12N 5/00* | (2006.01) | |
| *C12N 5/07* | (2010.01) | |
| *A61F 2/00* | (2006.01) | |

(52) U.S. Cl.
USPC ........... 435/177; 435/174; 435/176; 435/180; 435/182; 435/395; 424/422; 424/423

(58) Field of Classification Search
None
See application file for complete search history.

(56) References Cited

U.S. PATENT DOCUMENTS

| | | |
|---|---|---|
| 4,189,534 A | 2/1980 | Levine |
| 4,824,946 A | 4/1989 | Schwengers |
| 4,906,577 A | 3/1990 | Armstrong |
| 5,073,491 A | 12/1991 | Familletti |
| 5,153,133 A | 10/1992 | Schwarz |
| 5,175,093 A | 12/1992 | Seifert |
| 5,512,474 A * | 4/1996 | Clapper et al. ............... 435/402 |
| 5,654,197 A | 8/1997 | Jem et al. |
| 5,900,207 A | 5/1999 | Danforth |
| 5,916,585 A | 6/1999 | Cook |
| 6,150,581 A | 11/2000 | Jiang |
| 6,231,879 B1 | 5/2001 | Li |
| 6,261,493 B1 | 7/2001 | Gaylo |
| 6,287,558 B1 * | 9/2001 | Lanza et al. ................ 424/93.7 |
| 6,645,412 B2 | 11/2003 | Priedeman |
| 6,712,850 B2 | 3/2004 | Vyakarnam |
| 6,730,252 B1 | 5/2004 | Teoh |
| 7,485,670 B2 * | 2/2009 | Ruberti et al. ............. 514/772.2 |
| 2004/0010320 A1 | 1/2004 | Huckle |
| 2005/0221485 A1 | 10/2005 | Bader |
| 2006/0105011 A1 | 5/2006 | Sun |
| 2006/0154365 A1 | 7/2006 | Ratcliffe |
| 2006/0205071 A1 * | 9/2006 | Hasson et al. ............... 435/366 |

FOREIGN PATENT DOCUMENTS

| | | |
|---|---|---|
| WO | WO 2004/012782 | 2/2004 |
| WO | WO 2005/057436 | 5/2006 |
| WO | WO 2006/093778 | 9/2006 |

OTHER PUBLICATIONS

Wang et al., "Precision Extrusion Deposited Poly Epsilon-Coprolactone Structures for Biological Applications Specification." 2004, Rapid Prototype Journal 10(1):42-49.

* cited by examiner

*Primary Examiner* — David M Naff
(74) *Attorney, Agent, or Firm* — Saul Ewing LLP; Kathryn Doyle

(57) ABSTRACT

In on aspect, the invention includes a microcarrier bead having a porous three-dimensional core having (a) a polymeric porous three-dimensional body having porosity of about 15 to about 90% such that at least 99% of pores are interconnected and have diameters of at most 200 microns, (b) an outer protective layer and optionally (c) a filler. In another aspect, the invention includes a method of making an artificial scaffold wherein a scaffolding material is extruded into a coolant and thereby creating a porous material having a porosity of between 15-90% such that at least 99% of pores are interconnected and have diameters of at most 200 microns.

6 Claims, 6 Drawing Sheets

METHOD FOR MAKING ARTIFICIAL SCAFFOLD HAVING POROUS THREE-DIMENSIONAL BODY COMPRISING CELLS

CROSS-REFERENCE TO RELATED APPLICATIONS

This application is a divisional of U.S. patent application Ser. No. 11/842,796 filed Aug. 21, 2007, now pending, which is a U.S. national phase application filed under 35 U.S.C. §371 based on International Patent Application No. PCT/US2006/006790, filed Feb. 24, 2006, which is entitled to priority under 35 U.S.C. §119(e) to U.S. Provisional Patent Application No. 60/656,258, filed Feb. 25, 2005, and U.S. Provisional Patent Application No. 60/656,505, filed Feb. 25, 2005, all of which are incorporated by reference in their entirety herein.

BACKGROUND OF THE INVENTION

1. Field of Invention

This invention relates to microcarrier beads for use in bioreactors and methods for growing cells, specifically anchorage dependent cells, upon porous structures. Further, this invention relates to methods of creating scaffolds for artificial tissues and also the scaffolds and tissues made by these methods.

2. Description of Related Art

Anchorage dependent cells are difficult to culture to commercial yields because they cannot grow in suspension. Mammalian cells, most of which are anchorage dependent, require the presence of oxygen, but they are highly sensitive to the shear and bubbles created by the fluid motion and sparging required for creating a high dissolved oxygen count.

The ability to grow mammalian cells is important for academia and industry to produce biological agents and biomaterials such as, for example, proteins, hormones, vaccines, antibodies, antibiotics, insulin, etc. Mammalian cell growth in bioreactors can be facilitated with microcarrier beads, allowing for increased yields. Bioreactors and microcarrier beads have been described in U.S. Pat. No. 5,073,491 to Familletti, U.S. Pat. No. 5,175,093 to Seifert, U.S. Pat. No. 5,654,197 to Jem, et al., U.S. Pat. No. 5,153,133 to Schwarz, et al., U.S. Pat. No. 4,906,577 to Armstrong, et al., U.S. Pat. No. 4,824,946 to Schwengers, et al., U.S. Pat. No. 4,189,534 to Levine, et al., and U.S. Pat. No. 6,150,581 to Jiang, et al. CULTISPHER (Percell Biolytica AB, Sweden) beads are constructed of porous gelatin, with random pore orientation and unpredictable interconnectivity of pores. However, these microcarrier beads do not provide the protection from an agitated fluid environment to allow aggressive oxygenation of the suspension and hence higher cell yields; it is recommended stirring be only active enough to prevent CULTISPHER beads from sedimenting. CYTODEX is another type of microcarrier beads, which also does not provide sufficient cell survival at a more agitated fluid environment, as CYTODEX beads are non-porous beads, which grow anchorage dependent cells upon their surface.

Despite the foregoing developments, there is a need in the art for improved microcarrier beads capable of supporting cell growth in agitated conditions and providing larger areas for cell growth. Such beads would increase anchorage dependent cell yield in bioreactors as they would allow for increased suspension oxygenation due to stirring and sparging.

Three-dimensional (3D) scaffolds play important roles in scaffold guided tissue engineering because they provide critical functions as artificial extracellular matrices onto which cells can attach, grow, and form new tissues. Design and fabrication of tissue scaffolds are important issues in regenerative medicine, particularly for load bearing scaffolds in bone and cartilage tissue engineering application (see U.S. Pat. No. 5,900,207 to Danforth et al., U.S. Pat. No. 6,712,850 to Vyakamam et al., U.S. Pat. No. 6,730,252 to Teoh et al., and U.S. Pat. No. 6,645,412 to Friedman Jr.).

To design a 3D scaffold, one needs to address multiple biological, mechanical and geometrical design constraints and take into account scaffold external and internal geometry, porosity, pore size, pore interconnectivity, strength, transport properties, and microenvironment for cell and tissue ingrowth and healing (Hollister et al., 2002; Hutmacher, 2000; Sun and Lal, 2002). Advances in computer-aided tissue engineering and the use of biomimetic design made possible the introduction of biological and biophysical constraints into the scaffold design (Sun et al., 2003). However, thusly designed scaffolds often have intricate architectures that can only be fabricated through advanced manufacturing techniques. Most available scaffold fabrication methods, such as solvent casting, fiber bonding, phase separation, gas induced foaming, and salt leaching, either produce scaffolds with simple geometry or depend upon an indirect casting method for scaffold fabrication (Taboas et al., 2003; Yang et al., 2002). They are impractical for manufacturing scaffolds with complex structural architectures, and specifically complex internal architectures. To overcome this hurdle, solid freeform fabrication techniques, such as 3D printing, multi-phase jet solidification, and fused deposition modeling (FDM) have been widely adopted for scaffold fabrication (Koch et al., 1998; Wu et al., 1996; Zein et al., 2002). Among the reported techniques, FDM-based extruding deposition seems to be one of the most promising processes because of its versatility in using different scaffolding materials and the possibility of manufacturing scaffolds in a cell-friendly environment (Vozzi et al., 2002; Xiong et al., 2001). On the other hand, the ability to quantify the effect of the process on the morphology and the functional properties of the scaffolds is as important as the scaffold fabrication itself, because the biological and mechanical functions of the scaffold are in part dominated by the fabricated local micro-architecture of the scaffold. Micro-computed tomographic (micro-CT) imaging technology enables the characterization of the salient features of the scaffolds for tissue engineering applications. Recent reports have shown that micro-CT techniques are capable of characterizing micro-architectural and mechanical properties of tissue scaffolds (Lin et al., 2003), evaluating porous biomaterials (Muller et al., 1996), quantifying bone tissue morphologies and internal stress-strain behavior (Van et al., 1999), and conducting nondestructive evaluation for tissue properties (Muller and Ruegsegger, 1997). A recent study demonstrated the use of a precision extruding deposition (PED) process to fabricate poly-E-caprolactone (PCL) tissue scaffolds with designed micro-architecture, and then demonstrated the use of a micro-CT technique for evaluation and characterization of the morphologies and microstructures of the PED fabricated scaffolds. In contrast to the conventional FDM process that requires the use of precursor filaments, the PED process directly extrudes scaffolding materials from a granulated or pellet form without prior filament preparation.

An apparatus comprising a multi-nozzle biopolymer deposition system capable of extruding biopolymer solutions and living cells for freeform construction of three-dimensional tissue scaffolds is described in a PCT application Serial No. PCT/US2004/015316 filed on May 14, 2004 and U.S. patent application Ser. No. 10/540,968 incorporated herein in their entireties. The apparatus and the method do not describe depositing polycaprolactone (PCL).

The most common process of creating biocompatible structures is mold fabrication. While mold fabrication can create structures of desirable exterior shape, there is limited ability in controlling internal architecture. Secondary processes (such as salt fusion and phase manipulation) may be used to add porosity, but such processes often create random pores with unknown connectivity.

Currently, commercial applications of tissue engineering scaffolds are limited. Examples include films and gels such as those used in wound healing applications and rigid, porous filler materials such as those used to fill bone defects. Existing techniques need improvement when manufacturing of, tissue engineering scaffolds containing intact viable biomaterial is attempted.

Despite the foregoing developments, there is a need in the art for improved methods and apparatuses capable of producing porous structures with controllable pore sizes and pore interconnectivity, as well as the ability to incorporate biomaterial in a scaffold without affecting the biomaterial's viability.

All references cited herein are incorporated herein by reference in their entireties.

BRIEF SUMMARY OF THE INVENTION

The present invention provides a microcarrier bead comprising a porous three-dimensional core having (a) a polymeric porous three-dimensional body having porosity of about 15 to about 88% such that at least 99% of pores are interconnected and have diameters of less than 200 microns, preferably, less than 100 microns and (b) an outer protective layer.

In one aspect, the invention is a microcarrier bead comprising a porous three-dimensional core having (a) a polymeric porous three-dimensional body having porosity of about 15 to about 90% such that at least 99% of pores are interconnected and have diameters of at most 200 microns, (b) an outer protective layer and optionally (c) a filler material.

In certain embodiments, the porous three-dimensional core is made from a scaffold material comprising at least one of a biodegradable polymer, fibrin, collagen, and mixtures thereof.

In certain embodiments, the scaffolding material further comprises hydroxyapatite.

In certain embodiments, the scaffold material is at least one of poly-caprolactone, polylactic acid, polyglycolic acid, and poly(lactide co-glycolide).

In certain embodiments, the filler material is at least one of fibrin, collagen, and dextran.

In certain embodiments, the outer protective layer comprises hydrogel.

In certain embodiments, the scaffold material comprises a biodegradable polyester and the outer protective layer comprises alginate.

In certain embodiments, the porous three-dimensional core is made by depositing poly-caprolactone in a layered pattern such that at least 99% of pores is interconnected and at least 99% of pores lead to the external surface of the microcarrier bead.

In certain embodiments, the microcarrier bead of the invention, further comprises cells.

In another aspect, the invention is an assembly of more than two microcarrier beads.

In another aspect, the invention is method for making an artificial scaffold having porosity of about 15 to about 90% such that at least 99% of pores are interconnected and have diameters of at most 200 microns, the method comprising:
provoding a scaffolding material;
providing a coolant having a thermal conductivity of greater than 0.026; and
extruding the scaffolding material into the coolant and thereby making the artificial scaffold having a porous three-dimensional body wherein at least 99% of pores in the porous three-dimensional body are interconnected and lead to an external surface of the porous three-dimensional body and wherein pores have diameters of at most 200 microns.

In certain embodiments, extruding the scaffolding material into the coolant is performed in a layered pattern such that each subsequently extruded layer of the scaffolding material is deposited on top of a previously extruded layer of the scaffolding material.

In certain embodiments, the artificial scaffold comprises an artificial tissue.

In certain embodiments, the coolant is at least one of a liquid, a foam, and a hydrogel.

In certain embodiments, at least one of the scaffolding material or the coolant comprises a biomaterial.

In certain embodiments, the coolant has a temperature at least 5° C. lower than the scaffolding material.

In certain embodiments, the method further comprises providing a filler to the porous three-dimensional body.

In certain embodiments, the method further comprises providing cells to the porous three-dimensional body with or without a filler.

In certain embodiments, the method further comprises encapsulating the porous three-dimensional body with an outer protective layer (with or without the filler).

In another aspect, the invention is an artificial tissue comprising a scaffold having a polymeric porous three-dimensional body having porosity of about 15 to about 90% such that at least 99% of pores are interconnected and have diameters of at most 200 microns. In certain embodiments, the artificial tissue comprises cells.

In another aspect, the invention is an improvement in a process for manufacturing an artificial scaffold comprising (a) utilizing a computer aided design program to design the artificial scaffold; (b) converting the computer aided design program designed artificial scaffold into a heterogeneous material and multi-part assembly model which can be used for multi-nozzle printing; and (c) printing the designed artificial scaffold using different nozzles, wherein the improvement comprising extruding a scaffolding material into a coolant having a thermal conductivity greater than 0.026, wherein the coolant has a temperature at least 5° C. lower than the scaffolding material and thereby making the artificial scaffold having porosity of about 15 to about 90% such that at least 99% of pores are interconnected and have diameters of at most 100 microns and optionally an outer protective layer encapsulating the artificial scaffold.

The scaffold material can also be combined with various additives to better suit the type of cell or tissue that is being used. For example, hydroxyapatite could be used when working with osteoblasts to create bone implant scaffolds. The scaffold could also be coated with proteins and receptors that facilitate cellular adhesion or migration onto the scaffold surface. Growth factors and other biologically active agents could also be included within the scaffold material.

Applications of the invention include construction of artificial scaffolds and tissue engineering scaffolds incorporating biomaterial during scaffold construction for research studies and clinical applications including implants for bone, cartilage, fibrous tissue, muscle, plastic surgery applications, and tissue transplants, and construction of carrier beads for culture of anchorage dependent cells.

In another aspect, the invention is method of growing cells, the method comprising: providing the microcarrier bead of the invention having cells; and providing a bioreactor having an agitation rate and a sparging rate beyond the shear limit of cells in suspension.

BRIEF DESCRIPTION OF SEVERAL VIEWS OF THE DRAWINGS

The invention will be described in conjunction with the following drawings in which like reference numerals designate like elements and wherein:

FIGS. 7A and 7B are SEM images of scaffolds with different layout pattern wherein FIG. 7A is a 0°/120° layout pattern and FIG. 7B is a 0°/90° layout pattern.

DETAILED DESCRIPTION OF THE INVENTION

Figure 1:
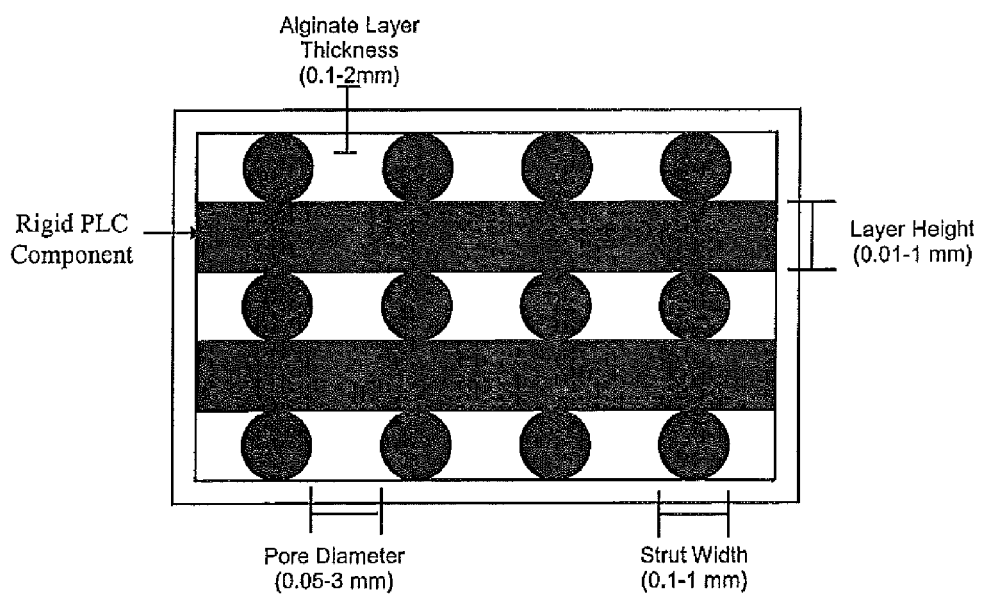
FIG. 1 is a scheme demonstrating a structure of a Super-Sparger microcarrier bead.

The invention relates to a microcarrier bead which comprises (a) a polymeric porous three-dimensional body having a customized porosity between 15-90% empty space by volume such that at least 99% of pores are interconnected and have diameters of less than 200 microns and preferably, less than 100 microns, (b) an outer protective layer and optionally (c) a filler. Advantageously, the microcarrier beads of the invention provide large amounts of protected surface area for cell attachment within the reactor. Bubble and fluid kinetic resistance is provided through an outer protective layer such as a thin hydrogel layer at the perimeter of the porous bead. Such high porosity was achieved by using a novel method as described in detail below.

The protective layer of the microcarriers of the invention also allows for a more agitated fluid environment than survivable by cells on known in the art (e.g., CYTODEX and CULTISPHER beads). CULTISPHER beads are constructed of porous gelatin, with random pore orientation and unpredictable interconnectivity. In the microcarrier beads of the invention, pore dimensions and nearly complete interconnectivity are known and measurable based on non-invasive micro-CT imaging and subsequent 3D image reconstruction of the beads. Pore dimensions and degree of interconnectivity are measured by image processing techniques of volumetric 3D reconstruction and region growing respectively. The outer layer allows diffusion of particles smaller than 1300 Daltons while providing mechanical resistance to fluid motion and preventing invasion of bubbles into the bead.

The microcarrier beads of the invention provide the needed porosity and protection from an agitated fluid environment to produce higher yields of anchorage dependent cells in a bioreactor due to the ability to withstand higher oxygen rates and feed of nutrients.

The microcarrier bead can further comprise a filler material in communication with the polymeric porous three-dimensional body. A filler material is a substance occupying the porespace of the microcarrier bead which allows passage of nutrients and volumetric cell seeding and attachment. The filler material must be biodegradable to allow replacement by growing extracellular matrix (ECM). In certain embodiments, the outer protective layer and the filler material are selected from the same materials. An example of a filler material is fibrin, introduced into the porespace of a microcarrier bead as fibrinogen and thrombin liquids, which then solidify into a hydrogel.

Advantages of the microcarrier beads of the invention over currently known microcarriers include greater surface area than that of the existing non-porous microcarriers, greater surface area due to the smaller pore size and interconnectivity over existing porous microcarriers, and ability of surviving agitated environment, hence greater nutrient transfer.

The invention will be useful for industrial scale pharmaceutical production of cells and manufacture of biomaterials such as, for example, proteins, hormones, vaccines, antibiotics, antibodies, insulin, etc. It will also be useful for academic or laboratory scale studies of cellular behavior.

Microcarrier beads of the invention can be used in a method for growing anchorage-dependent cells in a super-sparging bioreactor. The super-sparging bioreactor utilizes a conventional bioreactor but operates with more agitation and oxygen sparging than is normally used to provide the cells with oxygen and nutrients. An example of agitation is stirring of a suspension within a bioreactor using a mechanically driven propeller, a process which distributes nutrients through the biosuspension at a rate dependent upon propeller rotation. Excessive agitation is a rotation rate of the propeller that produces fluid flows and turbulence sufficient to kill or inhibit cells, reducing bioreactor yield. This shear sensitivity is highly variable by cell type. Oxygen sparging can be defined as the bubbling of gaseous oxygen through a biosuspension, frequently through a port beneath a mechanical propeller. Excessive oxygen sparging occurs when bubbles cause mechanical or chemical disruption of cells, also cell type specific, reducing bioreactor yield. The microcarrier beads of the invention (so-called Super-Sparger microcarrier beads) allow for higher agitation and sparging rates by growing the cells in a highly porous interior (i.e., interconnected pores) and protecting the bead with a layer of hydrogel, which allows nutrients in but protects against shear stress and bubbles. The porous Super-Sparger micro carrier beads present greater surface area than non-porous products such as CYTODEX beads due to the increased porosity. Due to the method used to manufacture the Super-Sparger beads together with the use of a coolant, the internal porosity is more uniform than that of the existing beads and pores are interconnected. The protective hydrogel layer allows for an environment with higher levels of dissolved oxygen than either existing porous or non-porous alternatives could withstand. The applications for these beads range from laboratory-scale bioreactors to simulate biological responses to mass production of pharmaceutical products such as insulin or antibodies.

The super-sparger bioreactor system includes a standard bioreactor system with a higher agitation rate and more rapid sparging than that used in standard reactors which allows delivering uniformly high concentrations of nutrients and oxygen to the cells. Whereas a standard mammalian cell fermentor might utilize an impeller rate of 150 rpm for mammalian cells, the super-sparger equivalent might operate at rates of 800 rpm, rates normally only possible for bacterial culture. Even though such conditions create an environment of shear stress and rapid bubbling which is hostile to mammalian cell growth, due to the novel design of the microcarriers of the invention, anchorage-dependent cells are protected from this environment on microcarrier beads constructed of porous precision extrusion deposited scaffolds (e.g., PCL) and a thin coating of hydrogel (e.g., alginate) on the exterior of the beads.

The pore space of the scaffold, 15-90% porosity with greater than 99% of those pores contiguous, provides surface attachment area for cells, and the hydrogel coating provides a continuous diffusion of oxygen and nutrients into the scaffold while providing mechanical resistance to fluid motion and preventing invasion of bubbles into the bead. This system facilitates the growth of high density culture of mammalian cells in bioreactors, cells which are difficult to culture due to shear sensitivity, high oxygen demand, and inability to grow in suspension. The rapid bubbling and agitation of the super-sparger/microcarrier bead system fulfills oxygen demand while protecting the cells from shear. The 3-dimensionality of the microcarrier bead interior mitigates the inability of the anchorage-dependent cells to grow in suspension. Any number of beads may be used in a given system, providing desired scaleability.

The microcarrier bead comprises at least two components, the core and the surrounding outer layer (see FIG. 1). Preferably, the core includes freeform fabricated poly-epsilon-caprolactone (PCL) deposited in a layered pattern such that >99% of the pore space is interconnected, and all pores lead to the external surface of the bead. If no filler material is used, the PCL struts of the core constitute the cell attachment surface of the microcarrier bead. The size and surface area of these struts are variable, based upon freeform fabrication parameters including nozzle aperture size, lateral speed, and pressure behind the nozzle. For example, strut width can range from about 100 microns to about 1,000 microns, preferably from 100 microns to 800 microns; pore diameter is from about 50 microns to about 3 mm. In certain embodiments, alginate layer's thickness is from 0.1 mm to 2 mm. Advantageously, then the coolant is employed, scaffolds with pores having diameters less than 200 microns (e.g., lass than 100 microns) can be obtained, which was not possible without the coolant. The method is versatile and allows creating larger pores with diameters larger than 200 microns if desired For an alternative cell attachment substrate, the porous PCL core may be filled with a filler material suitable for a selected cell type. Exemplary filler materials include fibrin, collagen, and dextran. The filler liquid may be gelated through addition of a crosslinking agent, calcium chloride solution for alginate and thrombin for fibrinogen. The resulting alginate or fibrin hydrogel provides cell attachment volume while maintaining potential for nutrient transfer. Other applications of this filler material include factor release and diffusion networks within the scaffolds. Hydrogel filler materials may be functionalized using methods known in the art.

Other variable parameters of the microcarrier bead include external geometry (size and shape) and internal porosity. The external size and pore size is variable, based upon the specific usage. For instance, 1 mm cubes with 80-100 micron pores could be used for cells that grow at high density and require great surface area, while 5 mm cubes with 800-1000 micron pores could be used for cells requiring greater rates of nutrient transfer. There is a three order of magnitude difference in the amount of oxygen that different cell types consume, so various types of carrier beads can be made.

All super-sparger microcarrier beads have a thin (~200 micron) layer of hydrogel, for example, alginate, surrounding the exterior of the bead. The function of this layer is to transfer oxygen from the heavily sparged medium to the cell attachment core while protecting against bubble intrusion and mechanical forces. This layer must be added after cells have been seeded within the core, but, once added, it would isolate the cell population. As an example, an alginate hydrogel layer may be used as the protective layer over a polycaprolactone core. Such a bead would be produced by creating the core using freeform fabrication, seeding the bead with the desired cell type, and then adding the alginate hydrogel through sequentially dipping the bead in sodium alginate and calcium chloride solutions.

Any hydrogel that allows diffusion of oxygen may be used, but materials that do not allow cell attachment will last longer and are preferred. A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazenes, and polyacrylates such as hydroxyethyl methacrylate (HEMA), which are crosslinked, ionically bound, or bound block copolymers such as PLURONICS or TETRONICS, polyethylene oxide-polypropylene glycol block copolymers which are crosslinked by temperature or pH, respectively. Other materials include proteins such as fibrin, polymers such as poly(vinylpyrrolidone), hyaluronic acid and collagen. Preferred examples of hydrogel include alginate, collagen, chitosan, fibrin, hyaluronic acid, agar, polyethylene glycol and its copolymers, acrylamide-based polymers, and acrylic acid-based polymers.

In preferred embodiments, the hydrogel is a member selected from the group consisting of alginate, collagen, chitosan, fibrin, hyaluronic acid, agar, polyethylene glycol and its copolymers, and acrylamide-based and acrylic acid-based polymers. Alginate is preferred for its immediate gelation kinetics, strong mechanical properties, fast diffusion of small molecules, and resistance to attachment by mammalian cells. Alginate's deficit is that it naturally biodegrades on a timescale of months, limiting the duration of its bioreactor applications. The term "alginate" shall refer to any of the conventional salts of algin, a polysaccharide of marine algae which may be polymerized to form a matrix for use within the growth chamber of the bioreactor. The salts of algin shall include, but are not limited to, any metal salt such as sodium, magnesium, etc. Preferably, the alginate includes, but is not limited to, a composition of gulronic and mannuronic acids possessing a low viscosity.

Porosity of the microcarrier bead of the invention is from about 15% to about 90%, preferably, from 30% to 88%.

Non-limiting examples of the scaffold material are polymers such as poly(caprolactones), polylactic acid), and poly-lactic-co-glycolic acid) (PLGA), fibrin, collagen, and other biologically useful materials which melt at temperatures of less that 200° C. without denaturing and which are capable of being processed by a freeform fabrication process. A mix of scaffold materials can also be used such as, for example, PCL with hydroxyapatite (HA) particles embedded as an additive. The scaffold materials are preferably biocompatible.

In preferred embodiments, the hydrogel is a member selected from the group consisting of alginate, collagen, chitosan, fibrin, hyaluronic acid, agar, polyethylene glycol and its copolymers, and acrylamide-based and acrylic acid-based polymers, and the scaffold material is a member selected from the group consisting of polycaprolactone, tricalcium phosphate, hydroxyapatite, polyglycolic acid, polylactic acid, co-polymers of polyglycolic and polylactic acid, poly-hydroxybutyrate, and polypropylene fumarate. The scaffold material can have a wide range of biodegradability, depending on the desired properties and purpose of the scaffold.

The super-sparger microcarrier beads are intended for anchorage-dependent, aerobic cells. The term "anchorage-dependent cells" shall refer to any cells, particularly mammalian cells, or cultures derived there from which will grow and multiply when attached to a support material, and shall include, but is not limited to, cells which will only grow when attached to a solid support material. A potential use includes culture of secretory cells such as pancreatic islet cells for large-scale production of drugs such as insulin. Through use of a filler material, non-anchorage-dependent cells could also be cultured, including prokaryotes such as *Escherichia coli* (*E. coli*), which are already used in pharmaceutical manufacture processes.

As an example of use of super-sparger micro-carrier beads, hybridomas bred to produce insulin could be produced at great density and high product yield using enhanced agitation and sparging. Hybridomas are shear-sensitive cells which can be grown in suspension in standard culture. A standard fermentor impeller might operate at 150 rpm in maintaining hybridomas. The growth strategy using super-sparger microcarrier beads would be to seed them into the microcarrier beads prior to culture, protect those micro-carrier beads with a hydrogel layer such as alginate, and to operate the fermentor at impeller rates of over 800 rpm, normally a rate only possible with bacteria. The increased rate would lead to improved nutrient distribution within the biosuspension volume. Given a similar solute utilization rate in encapsulated hybridomas to hybridomas in suspension, total insulin product yield would be increased.

In another aspect, the invention is a method for making an artificial scaffold having a customized porosity between 15-90% by volume such that at least 99% of pores are interconnected and have diameters of at most 200 microns and preferably, 100 microns.

The inventors have discovered that utilizing an integrated cooling step provides a method for construction of porous structures with controllable smaller pore sizes and enhanced interconnectivity and ability to incorporate a biomaterial in a scaffold without affecting the biomaterial's viability due to the high temperature of the melt. The use of a coolant with the PED system further enhances scaffold criteria such as strut and pore width. These porous criteria are important for biological applications. The pore interconnectivity allows nutrient transfer to cells cultured on these structures, porosity effects nutrient transfer and surface area for cell attachment, and pore size affects the behavior of specific cell types. The specific applications for these structures include tissue engineering scaffolds and cell culture microcarrier beads.

The inventors have discovered that extruding into a coolant to expedite phase transition allows for creation of pores 100 microns or less in size. A consistent mesh-like deposition pattern allows for ~100% porous interconnectivity. Any material may be used with a melting point within the range of the heating element, allowing for use of biocompatible materials such as poly-epsilon-caprolactone (PCL).

Precision Extrusion Deposition (as previously described by inventors in the article by Wang, et al., "Precision Extrusion Deposited Poly-Epsilon-Caprolactone Structures for Biological Applications Specification", Rapid Prototype Journal, Vol. 10, No. 1, pp. 42-49, 2004 and presented at the 14th Annual Solid Freeform Fabrication Symposium, University of Texas, Austin, Tex., 4-6 Aug. 2003) forces powder or pellets of material through a heating element where it is melted and extruded out from a micro-scale nozzle with pressure generated by a rotating screw. The extruded materials are guided by nozzles and solidified as strands of small diameter. Mounted on a 3D positioning system, the extrusion head may deposit these strands at any width, or fill gap, apart from each other. Once a layer is complete, the extrusion head is moved upwards one increment, or layer height, and more strands are deposited at a variable angle to the previous layer. Control of fill gap allows fine control of porosity. Control of fill gap and layer height allows fine control of pore size.

Figure 2:
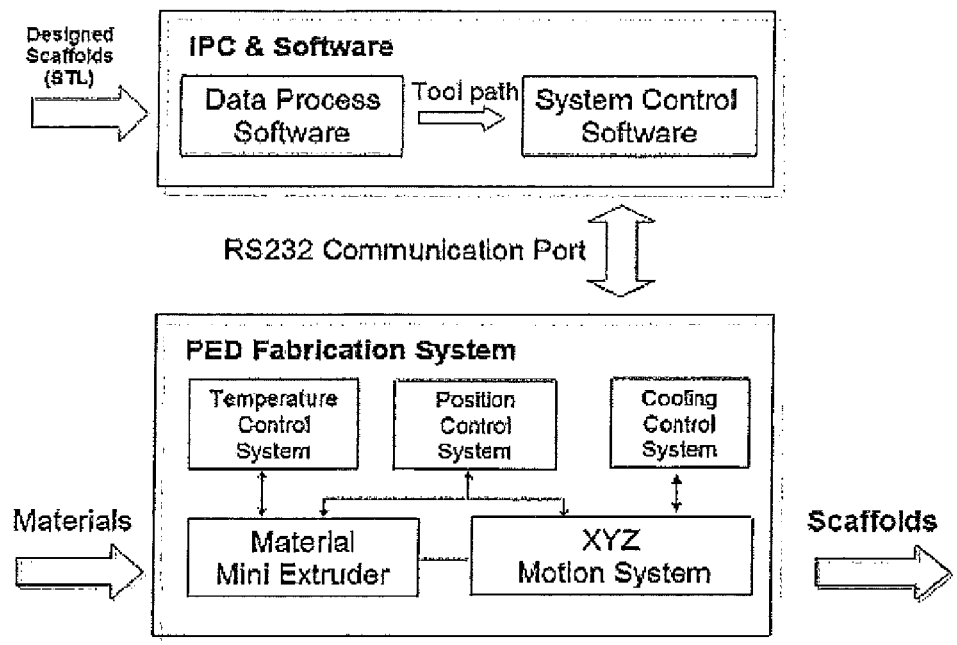
FIG. 2 is a scheme demonstrating configuration of the PED system.

A schematic configuration of the PED system (Bellini, 2002) is shown in FIG. 2. The hardware component consists of an XYZ positioning system, a material extruder system, and a temperature control system. The software component consists of data processing software and system control software. The data processing software slices the STL files and generates the process toolpath. The system control software controls the material deposition according to the process toolpath to form a layered 3D object. Researchers from the University of Singapore reported a fused deposition method utilizing a polymeric filament, which is fed into the extrusion head. They did not use a coolant and the resultant scaffold struts were significantly larger than the ones disclosed herein. In the invention, the PED system forces pellets of PCL, rather than a filament, through a set of heating elements, wherein the pressure is generated by a rotating screw. The pressure generated is greater allowing for smaller nozzles and smaller strut sizes and thereby allowing the creation of higher porosity scaffolds, smaller individual pore sizes, and smaller architectural features. The use of PCL pellets as a feed material also negates the necessity of a second machine to create the sort of filament used in fused deposition.

Figure 3:
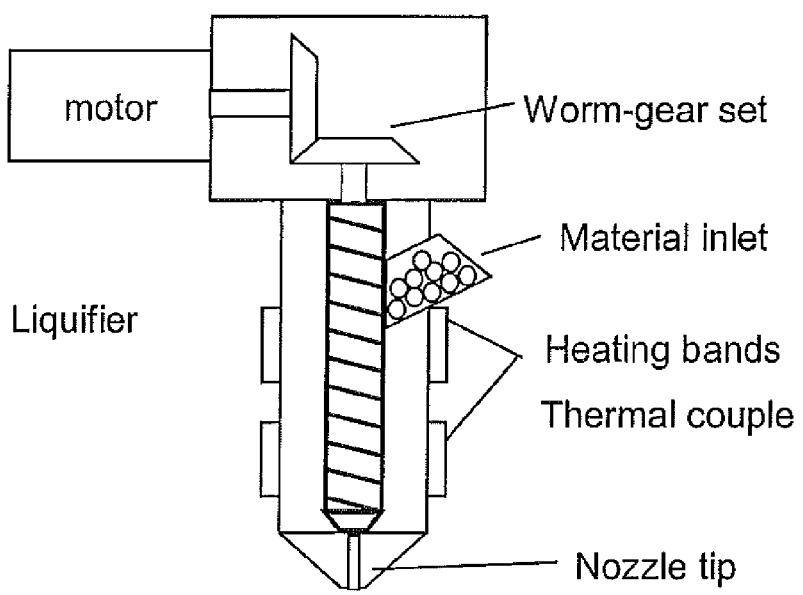
FIG. 3 is a scheme demonstrating an extruder nozzle.
Figure 4:
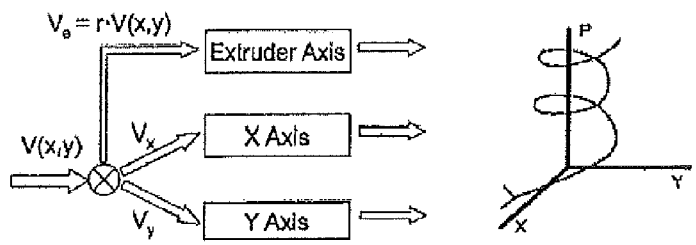
FIG. 4 is a scheme demonstrating synchronization of positioning and material dispensing system.
Figure 5:
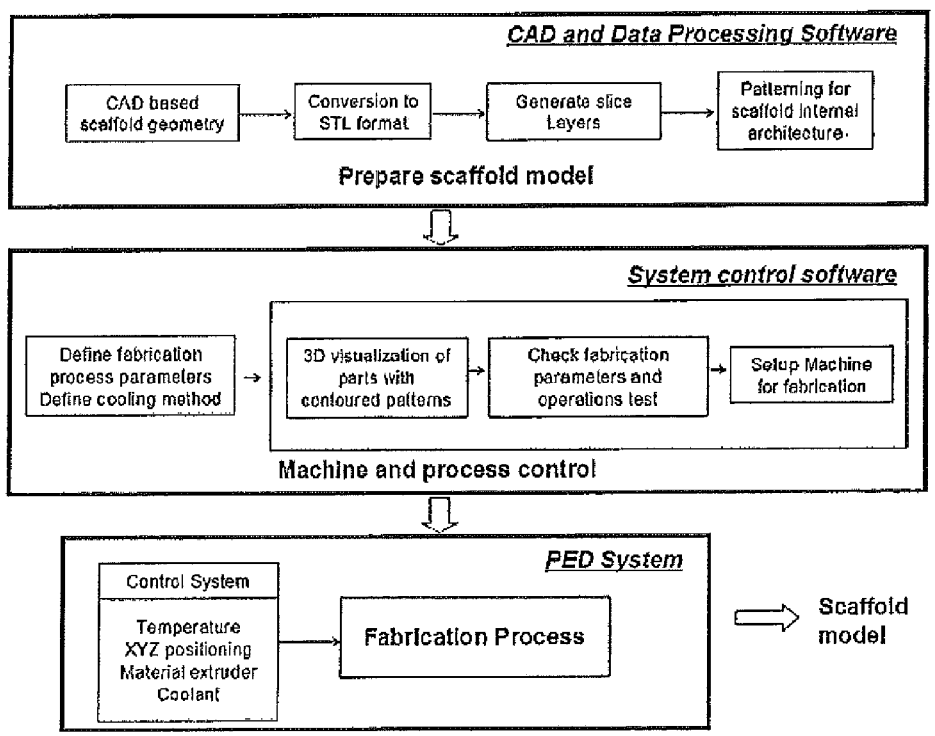
FIG. 5 is a scheme demonstrating the information process of the PED system.

The material mini-extruder system delivers the scaffold material in a fused form through the deposition nozzle. The major difference of the PED process with the conventional FDM process lies in that the scaffolding material can be directly deposited through PED process without involving pre-process filament preparation. The pellet formed PCL is fused by a liquefier temperature created by two heating bands and maintained by respective thermocouples, and then the material is extruded by a pressure created by a turning precision screw. A schematic of the material mini-extruder system is shown in FIG. 3. To achieve deposition accuracy, the positioning system and the material mini-extruder are synchronized as shown in FIG. 4. The material deposition roads (of both contouring and raster filing) consist of series of line segments, so the extruder movement is composed of a series of 2D linear interpolations upon which a simultaneous proportional signal to the XY position is extracted. The signal is used to drive the rotating motor of the material extruder. The proportional ratio can be adjusted to coordinate the positioning system and material dispensing system according to its controlled movement, speed, and material extrusion flow rate. FIG. 5 shows the information pipeline during the fabrication process. The designed scaffold CAD model is first converted into STL format, and then sliced with each slice pattern stored in the pattern library for toolpath generation. Initialized by a parameters file, the in-house developed system control software provides functions for 3D part visualization, machine and process setup, testing and monitoring during the real-time fabrication process.

PCL (Sigma Aldrich Inc., Milwaukee, Wis.) in the form of pellets was used as the scaffolding material. PCL is a semi-crystalline aliphatic polymer that has a slower degradation rate than most biopolymers in its homopolymeric form. PCL has a low glass transition temperature of −60° C., a melting temperature of about 58-60° C., and a high thermal stability. PCL has a high decomposition temperature (Td) of 350° C. The mechanical properties of PCL (MW=44,000) are as follows: a tensile strength of 16 MPa, tensile modulus of 400

MPa., flexural modulus of 500 MPa, elongation at yield of 7.0%, and elongation break of 80%.

The Precision Extrusion Deposition system with a cooling step, is an improvement to the previously disclosed Precision Extrusion Deposition system and provides an in-situ cooling step, wherein a coolant is used to speed up the physical solidification of scaffolding materials and provide milder temperatures for incorporating biomaterials simultaneously with depositing scaffolding materials.

Inventors have discovered that a biomaterial sensitive to elevated temperatures (i.e., above 37° C.) can be deposited together with the scaffolding material (e.g., PCL) without compromising its viability if the scaffolding material is cooled off during the deposition step. Without the additional cooling step, the scaffolding material is deposited on a surface at a room temperature as described in the article by Wang, et al., "Precision Extrusion Deposited Poly-Epsilon-Caprolactone Structures for Biological Applications Specification", Rapid Prototype Journal, Vol. 10, No. 1, pp. 42-49, 2004. Since the scaffolding material is being extruded at its melt temperature (about 60° C.), it will take time to cool off to 37° C. Advantageously, the additional cooling step involving using a coolant addresses these shortcomings and provides a method of making more viable biomaterial-containing scaffolds.

In certain embodiments, the scaffolding material is deposited in a layer of a coolant having a temperature of at least 5° C. lower than the scaffolding material and the filler material (if used), wherein the coolant is, for example, a liquid, a foam, or any material with a thermal conductivity greater than 0.026. An example of a liquid is water and an example of suitable foam is a surfactant. The coolant is preferably mixed with a biomaterial such as, for example, cells, proteins, pharmacologically active agents, a component of a substrate-ligand pair, etc.

The coolant is provided as a layer of a constant depth or multiple layers which can be added as needed during the deposition of the scaffolding material. In certain embodiments, the scaffolding material can be deposited simultaneously with the coolant, wherein the coolant is preferably mixed with biomaterial such as, for example, cells. During such deposition, the scaffolding material is being chilled along the outer parts of its extruded mass. A nozzle for depositing the scaffolding material is positioned adjacent to two or more nozzles for depositing a coolant. In another variant, the nozzle for depositing the scaffolding material is nested inside a larger nozzle for depositing the coolant.

The above described ways of introducing a coolant can be combined. More than one type of the scaffolding material can be deposited. The scaffolding material can be deposited with other non-scaffolding material such as, for example, a filler material (e.g., hydrogel) which can also act as a coolant in some embodiments.

Non-limiting examples of the scaffold material are poly (capralactones), poly(lactic acid), poly(lactic-co-glycolic acid) (PLGA), fibrin, collagen, hydroxyapatite (HA), and other biologically useful materials. The scaffold materials are preferably biocompatible.

In preferred embodiments, the hydrogel is a member selected from the group consisting of alginate, collagen, chitosan, fibrin, hyaluronic acid, agar, polyethylene glycol and its copolymers, and acrylamide-based and acrylic acid-based polymers, and the scaffold material is a member selected from the group consisting of polycaprolactone, tricalcium phosphate, hydroxyapatite, polyglycolic acid, polylactic acid, co-polymers of polyglycolic and polylactic acid, polyhydroxybutyrate, and polypropylene fumarate. The scaffold material can have a wide range of biodegradability, depending on the desired properties and purpose of the scaffold.

The scaffold material can also be combined with various additives to better suit the type of cell or tissue that is being used. For example, hydroxyapatite could be used when working with osteoblasts to create bone implant scaffolds. The scaffold could also be coated with proteins and receptors that facilitate cellular adhesion or migration onto the scaffold surface. Growth factors and other biologically active agents could also be included within the scaffold material.

The key steps of making the microcarrier beads of the invention by a freeform fabrication process will now be described. In a preferred embodiment, the freeform fabrication process is precision extrusion deposition. The process of precision extrusion deposition (PED) is described in PCT application Serial No. PCT/US2004/015316 filed on May 14, 2004 and U.S. patent application Ser. No. 10/540,968 incorporated herein in their entireties and the articles by Wang, et al., "Precision Extrusion Deposited Poly-Epsilon-Caprolactone Structures for Biological Applications Specification", Rapid Prototype Journal, Vol. 10, No. 1, pp. 42-49, 2004.

A porous block of PCL is fabricated using a PED system, wherein certain parameters are selected (e.g., materials, strut size and orientation, porosity of the resulting microcarrier bead, the resulting microcarrier bead's height). The porous block is cut into individual microcarrier beads based on desired external geometry of the microcarrier bead (cylinder, cube, etc.). A filler is introduced to the bead either through gelation of a liquid such as fibrinogen with thrombin or direct introduction of a low viscosity material such as collagen. If no filler is used, cells must still be seeded at this stage (e.g., by dipping the beads in the culture, by depositing cells onto the beads using, for example, a syringe).

The filler is optional and can be selected based on its function (e.g., for cell attachment or for cell immobilization). A film of hydrogel (e.g., alginate) is created over the bead (filled or unfilled) by sequential dipping in sodium alginate solution and calcium chloride, wherein parameters of the coating such as, for example, thickness of alginate coating and alginate concentration can be varied. Cells can be seeded after the filler material is deposited or simultaneously with the deposition of the filler. For example, cells can be mixed with fibrinogen and thrombin.

The microcarrier beads seeded with cells can be placed directly in the fermentor or kept cold or frozen if desired.

An exemplary method of making an artificial scaffold will now be described.

Figure 6A:
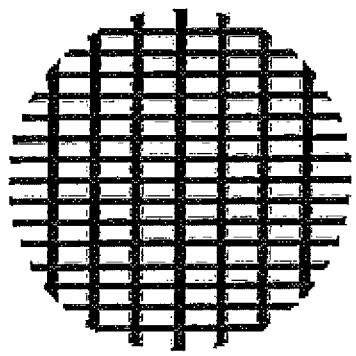
FIGS. 6A and 6B are schemes demonstrating scaffold layout patterns 0/90° and 0/120° respectively.
Figure 6B:
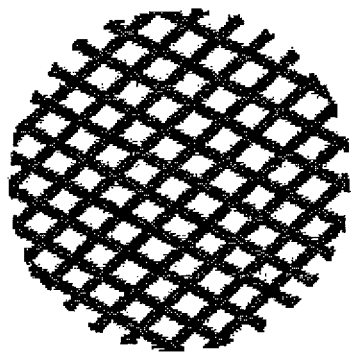

A scaffold cylinder model, measuring 20 mm in diameter and 10 mm in height, was first created in a CAD format. This cylinder CAD model was converted to a STL format then sliced into layers. Each layer was then filled with the designed scaffold pattern to generate a toolpath file. The strands of PCL were extruded in four distinct layer patterns: 0, 90, 60, and 120° (designated P1, P2, P3 and P4, respectively), or alternating layers of 60°/120° with different gap lengths between the strands. Scaffold layout patterns 0/90° and 0/120° are shown in FIGS. 6A and 6B respectively.

A set of PCL scaffolds was fabricated using the PED system. The following processing parameters were used for all scaffold fabrication: the processing liquefier temperature was 90° C., the orifice diameter of the tip was 0.25 mm, and deposition velocity was 20 mm/s. Filling gaps of 0.42 and 0.51 mm were applied for two different sets of scaffolds. For each scaffold, there were a total of 39 layers with each layer thickness at 0.254 mm. The scaffold patterns were either 0°/90° (three samples), or 0°/120° (three samples), or a combination of the two.

Figure 7A:
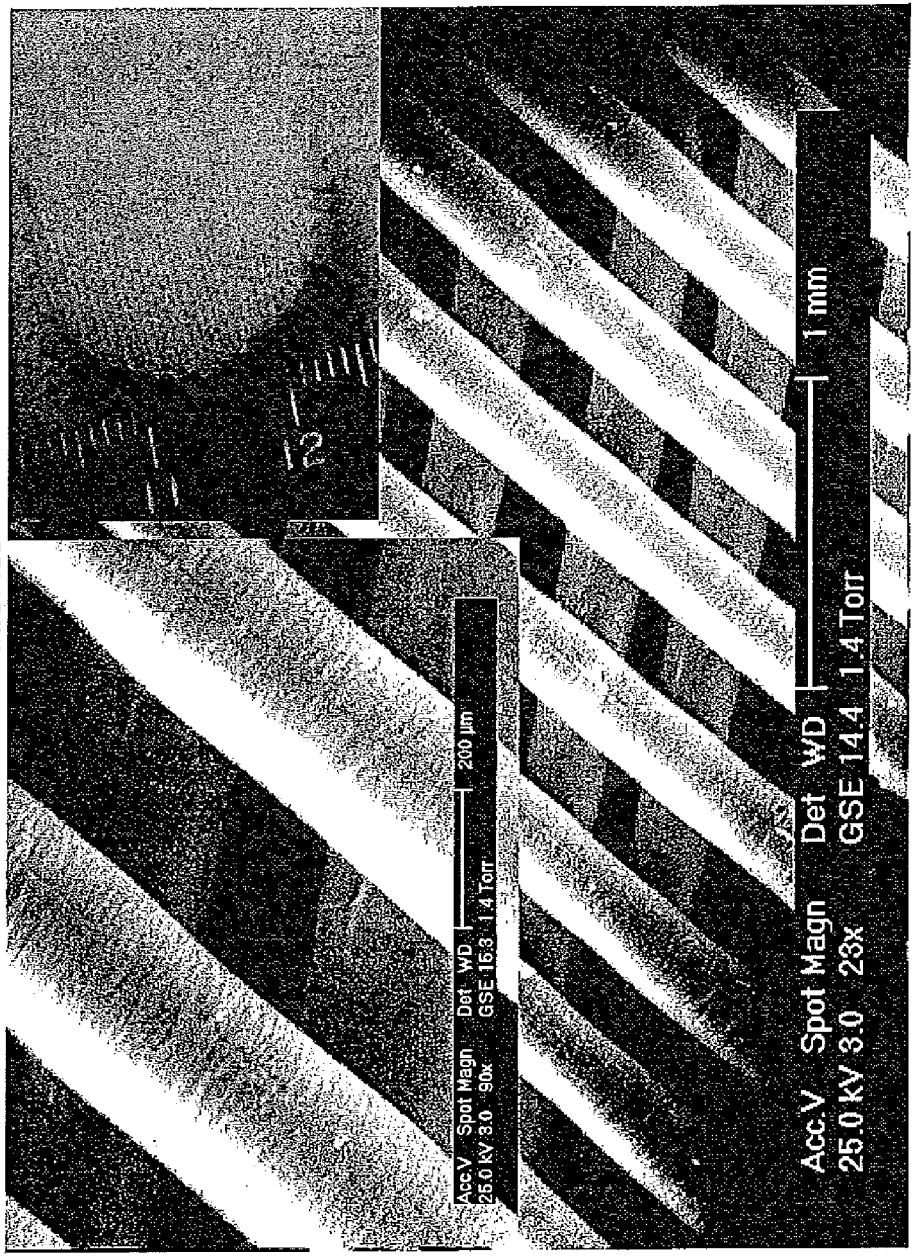
Figure 7B:
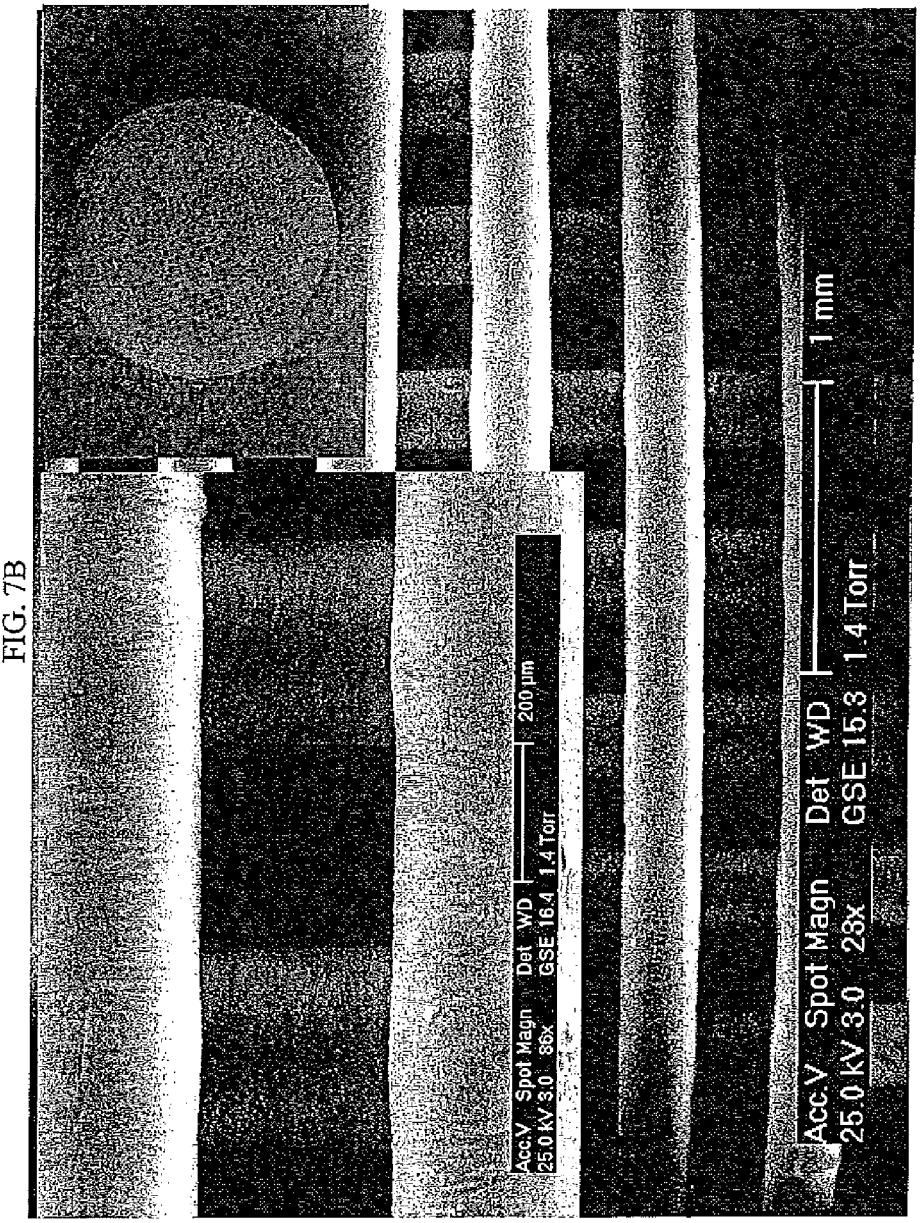

FEI/Phillips XL-30 field emission environmental scanning electron microscope (ESEM) was used to evaluate the microstructural formability and internal morphologies of as-fabricated scaffolds. The SEM images were taken using a beam intensity at 20.0 keV and the gaseous secondary electron detectors at 1.3 Torr. The SEM images of scaffolds are shown in FIG. 7A (for 0°/90° deposition pattern) and FIG. 7B (for 0°/120° deposition pattern), along with the images of the as-fabricated scaffolds. Both SEM images clearly show that the fabricated microarchitecture of the scaffolds is achieved at about 250 μm scale level. The good uniformity of the fill gaps and the deposited struts shown in FIGS. 7A and 7B, and the internal pore connectivity demonstrate the applicability of using the PED process to fabricate PCL scaffolds at the micro-scale level.

Micro-CT enables 3D characterization of the salient features, the structural formability and the morphologies of the as-fabricated PCL scaffolds. The micro-CT was set at 19.1 μm resolution. 2D analyses and 3D reconstructions of core regions of the sample scaffolds were performed. These results illustrate that qualitative and quantitative analysis of polymer scaffolds is possible through micro-CT and 3D reconstruction techniques.

A SkyScan 1072 micro-CT desktop scanner (Skyscan, Belgium) was used to scan the internal architecture of the scaffold. The output format for each sample was approximately 500 serial 1,024×1,024 bitmap images. These slice images were analyzed in SkyScan's Tview software. Initially, length measurements were taken around the sample to determine the degree to which the sample conformed to the cylindrical template. Volume analyses were performed on the center of each sample. Volume fraction and surface per unit volume were determined in 3D analysis, and relative area was measured in ten randomly selected slice images in 2D analysis. Ten strut and pore widths were measured in 2D images from each sample.

3D reconstruction was performed using Mimics software (Materialise, Belgium) with pre-processing using Image J. Sixty-two sequential 200×200 pixel images were cropped from the serial images from the center of each sample. Imported into Mimics, these serial core images were reconstructed into 3D volumetric models. Thresholds were inverted to allow measurement of the volume of all pore spaces within the model. Subsequently, a region-growing operation was performed, creating a mask consisting only of interconnected pore spaces. Volume for this region-grown mask was determined and the ratio of region-grown volume to the total volume was calculated. The percentage of this ratio is defined as the degree of porous interconnectivity.

The Instron 5800R machine was used for mechanical testing of the as-fabricated scaffolds. The initial strain rate of the tests was adjusted to 10%/min at the beginning of the test and no preload was applied before initiating compression testing. Standard solid compression platens were used for testing. Stress-strain data were computed from load and displacement measurements. Compressive modulus was determined based on the slope of the stress-strain curve in the elastic region.

Three SP-2 specimens were tested under compression to a limit of specific compressive displacements. The PCL specimens were measured for their dimensions for accurate area calculations. The scaffolds were cylindrically shaped with minute irregularities on the circumference wall due to specimen processing. The samples were compressed at a speed of 0.1 mm/min at a room temperature of 24° C. with a relative humidity of 15%.

Precision extrusion deposition (PED) is a freeform fabrication technology allowing for the construction of tissue engineering scaffolds and other bioactive structures with customizable macro- and microarchitectural characteristics. The ability to control porosity, pore size, and external shape is not found with the same flexibility in any alternative scaffold manufacturing technology. These capabilities are valuable in a number of research and commercial applications. The ability to create tissue engineering scaffold specimens with precise geometry is ideal for cell experimentation, in vivo experimentation, and studies of nutrient transfer. Potential clinical applications of such scaffolds include a range of regenerative medicine treatments including bone repair, cartilage repair, plastic surgery, dental repair, and eventually transplantation of complex tissues and organs. In terms of the bone market alone, 5-10% of all fractures are delayed healing or non-union and hence candidates for scaffold-based regenerative medicine. With the aging of the population, that is expected to rise to 20% by 2025. All gross tissue/organ replacement therapies in the world currently constitute a $300 billion annual market, with an estimated increase of 10-11% per year. PED fabricated biocompatible structures present a unique approach applicable to a broad range of these therapies.

Hydrogels such as fibrin and alginate present the potential for volumetric cell immobilization and attachment, but their mechanical properties are inherently weak, and the structures buildable through mold fabrication of hydrogels are limited. Suspension in a rigid framework makes hydrogels much more versatile for biological applications, but the framework itself must have finely controlled internal and external architecture. Once the rigid framework is constructed, alginate or fibrin may be gelled within the scaffold pores, allowing for volumetric cell immobilization and cell attachment. The ability to immobilize cells 3-dimensionally is ideal for uniformly seeding tissue constructs for clinical implantation. Hydrogel-filled PED fabricated biocompatible structures present a unique approach applicable to a broad range of these therapies.

In another aspect, the invention is an artificial tissue made by the method of the invention.

The term "artificial tissue" is used interchangeably with the term "engineered tissue" and include a scaffold made of biocompatible materials, which is designed to act as a prosthetic tissue (e.g., a patch or an implant) as well as a scaffold (e.g., ECM) combined with cells grown thereon, which will act as a native tissue.

Preliminary biological experiments have been conducted to study the basic scaffold biocompatibility. These experiments were intended to address the issue of free radicals caused by heating of the polymer and whether these radicals would be detrimental to cell growth. Another question was whether the pore size of approximately 250 μm would be conducive to cell growth alone or would require a filler material.

Cardiomyoblasts (H9C2) were seeded onto three sets of 90° scaffolds, one set with no filler material, one with collagen filling the pores, and one with fibrin gel filling the pores. Initial seeding size was approximately $10^5$. All samples showed cell attachment to the scaffold on the fifth day, and a monolayer of cells atop the scaffold sample. The confluence of the monolayer atop the scaffold on the fifth day indicates uninterrupted cell growth.

A study on using the PED process to freeform fabricate PCL scaffolds and on using SEM, micro-CT, and experimental testing to characterize the morphology, internal geometry, mechanical property, and biological compatibility of the as-fabricated scaffolds was conducted. Both hardware and software configuration of the PED process system were described and the PCL scaffolds with controlled internal architectures were produced. Results of the characterization demonstrated the capability of the PED fabrication process in manufacturing the PCL scaffolds with microstructure and pore size at about 250 µm scale. This process directly fabricates tissue scaffolds by converting designed architecture into a layered deposition pattern without involving material pre-processing and in-direct casting, and thus opens opportunities for complex scaffold fabrication. Results of the characterization also show that micro-CT is a capable tool for nondestructive evaluation of PCL scaffolds. The use of 2D analysis and 3D reconstruction software allows the examination of morphologies, internal architecture, the interconnectivity of as-fabricated tissue scaffolds, and provides a quantitative measurement of porosity and micro-architecture. As shown in the analysis, a typical pore size of the fabricated scaffolds ranges from 200 to 300 µm, near the optimal size suggested for bone tissue scaffold applications. In addition, strut width is consistent between samples, as all samples showed greater than 98 percent interconnectivity. The scaffold compression modulus obtained from the test was in the range between 150 and 200 MPa. The preliminary result of biological experiments demonstrated the biocompatibility of the process and material. All these suggest the viability of the fabrication and the characterization process, as well as its potential applications in tissue engineering.

The dominant approach in 3D tissue engineering is to construct a scaffold of biocompatible material, to seed the scaffold with an appropriate cell type, to culture these cells in a bioreactor, and to implant the resulting tissue construct. Numerous individual materials have been investigated, but no single material has proven ideal for tissue culture. Inventors propose the use of multiple materials within a single scaffold. Such scaffolds can be produced using a 3D positioning system possessing multiple heads, capable of both fused deposition and droplet deposition of multiple materials.

While the invention has been described in detail and with reference to specific examples thereof, it will be apparent to one skilled in the art that various changes and modifications can be made therein without departing from the spirit and scope thereof.

What is claimed is:

1. A method for making an artificial scaffold having a porous three-dimensional body comprising cells and having porosity of about 15 to about 90% such that at least 99% of pores are interconnected and have diameters of at most 200 microns, the method comprising:

providing a scaffolding material;

providing a layer of coolant comprising cells mixed with the coolant, wherein the coolant is at least one of a liquid, a foam, a hydrogel, and wherein the coolant has a temperature of at least 5° C. lower than a temperature of the scaffolding material, and has a thermal conductivity of greater than 0.026; and extruding the scaffolding material into the layer of coolant and thereby making the artificial scaffold having a porous three-dimensional body comprising cells wherein at least 99% of pores in the porous three-dimensional body are interconnected and lead to an external surface of the porous three-dimensional body and wherein pores have diameters of at most 200 microns.

2. The method of claim 1, wherein extruding the scaffolding material into the coolant is performed in a layered pattern such that each subsequently extruded layer of the scaffolding material is deposited on top of a previously extruded layer of the scaffolding material.

3. The method of claim 1, wherein the scaffolding material comprises at least one of a biodegradable polymer, fibrin, collagen, and mixtures thereof.

4. The method of claim 3, wherein the scaffolding material further comprises hydroxyapatite.

5. The method of claim 1, further comprising providing a filler to the porous three-dimensional body, wherein the filler is deposited with the scaffolding material.

6. The method of claim 1, further comprising encapsulating the porous three-dimensional body with an outer protective layer.

* * * * *